(12) United States Patent
Flippe et al.

(10) Patent No.: US 11,833,339 B2
(45) Date of Patent: *Dec. 5, 2023

(54) ADAPTOR FOR A DRUG DELIVERY DEVICE AND DRUG DELIVERY DEVICE

(71) Applicant: Becton Dickinson France, Le Pont de Claix (FR)

(72) Inventors: Marc Flippe, Claix (FR); Freddy Mills, Fontanil Cornillon (FR)

(73) Assignee: Becton Dickinson France, Le Pont de Claix (FR)

( * ) Notice: Subject to any disclaimer, the term of this patent is extended or adjusted under 35 U.S.C. 154(b) by 492 days.

This patent is subject to a terminal disclaimer.

(21) Appl. No.: 17/096,676

(22) Filed: Nov. 12, 2020

(65) Prior Publication Data

US 2021/0060267 A1  Mar. 4, 2021

Related U.S. Application Data

(63) Continuation of application No. 15/580,294, filed as application No. PCT/EP2016/063267 on Jun. 10, 2016, now Pat. No. 10,864,331.

(30) Foreign Application Priority Data

Jun. 12, 2015 (EP) .................... 15305915

(51) Int. Cl.
*A61M 5/34* (2006.01)
(52) U.S. Cl.
CPC ............ *A61M 5/344* (2013.01); *A61M 5/349* (2013.01); *A61M 5/347* (2013.01)

(58) Field of Classification Search
CPC ....... A61M 5/344; A61M 5/347; A61M 5/349
See application file for complete search history.

(56) References Cited

U.S. PATENT DOCUMENTS

| 4,266,815 | A | 5/1981 | Cross |
| 10,864,331 | B2 * | 12/2020 | Flippe .................. A61M 5/344 |
| 2005/0087715 | A1 | 4/2005 | Doyle |
| 2005/0096504 | A1 | 5/2005 | Akiba |

(Continued)

FOREIGN PATENT DOCUMENTS

| JP | 200720980 A | 2/2007 |
| JP | 200817987 A | 1/2008 |

(Continued)

*Primary Examiner* — Brandy S Lee
(74) *Attorney, Agent, or Firm* — The Webb Law Firm (57) ABSTRACT

The present invention relates to adaptor (30) for a drug delivery device having a reservoir (12) and a longitudinal tip (20), the adaptor (30) comprising a distal part defining a connecting ring (31) intended to receive a connector, and a proximal part defining a mounting ring (33) having an inner surface (34), the mounting ring (33) being shaped and configured such that, when the adaptor (30) is mounted around the longitudinal tip (20) of the drug delivery device, at least one annular space (38) is created between said inner surface (34) of the mounting ring (33) and said outer surface (20a) of the longitudinal tip (20), said at least one annular space (38) being able to accommodate an adhesive layer (40) in order to bond said adaptor (30) to said longitudinal tip. The invention further relates to a drug delivery device comprising such an adaptor.

18 Claims, 7 Drawing Sheets

(56) References Cited

U.S. PATENT DOCUMENTS

| | | |
|---|---|---|
| 2008/0132851 A1 | 6/2008 | Shaw et al. |
| 2009/0131864 A1 | 5/2009 | Pickhard |
| 2012/0029438 A1 | 2/2012 | Vernizeau et al. |
| 2012/0157928 A1 | 6/2012 | Mermet |
| 2012/0258421 A1 | 10/2012 | Selvitelli et al. |
| 2013/0178806 A1 | 7/2013 | Felix-Faure et al. |
| 2016/0143811 A1 | 5/2016 | Poncon et al. |
| 2016/0158518 A1 | 6/2016 | Hallynck et al. |
| 2016/0250420 A1 | 9/2016 | Maritan et al. |

FOREIGN PATENT DOCUMENTS

| | | |
|---|---|---|
| WO | 2010052517 A1 | 5/2010 |
| WO | 2010140019 A1 | 12/2010 |

* cited by examiner

ADAPTOR FOR A DRUG DELIVERY DEVICE AND DRUG DELIVERY DEVICE

CROSS REFERENCE TO RELATED APPLICATIONS

This application is a continuation of U.S. patent application Ser. No. 15/580,294, filed Dec. 7, 2017, which is the United States national phase of International Application No. PCT/EP2016/063267, filed Jun. 10, 2016, and claims priority to European Patent Application No. 15305915.9, filed Jun. 12, 2015, the disclosures of which are hereby incorporated in their entirety by reference.

BACKGROUND OF THE INVENTION

The present disclosure relates to an adaptor, in particular a luer lock adaptor for use with a drug delivery device having a reservoir and a longitudinal tip, the adaptor being able to be bonded around the longitudinal tip of the drug delivery device in order to connect the drug delivery device with a connector such as an injection needle or an intravenous line. The present disclosure also relates to a drug delivery device comprising such an adaptor.

In this application, the distal end of a component or apparatus must be understood as meaning the end furthest from the hand of the user and the proximal end must be understood as meaning the end closest to the hand of the user, with reference to the drug delivery device intended to be used with said component or apparatus. As such, in this application, the distal direction must be understood as the direction of injection with reference to the drug delivery device, and the proximal direction is the opposite direction to said direction of injection.

Drug delivery devices are widely used by medical staff and patients to store and/or administer and/or transfer medical compositions such as drugs, vaccines, cosmetics or diagnostics liquids. They can take the form of a cartridge or a syringe, both types of devices comprising a reservoir for storing the medical composition. Drug delivery devices are preferably made of glass for its high chemical passivity, its low gas permeability and high transparency, which allows an extended storage and an easy inspection. Drug delivery devices such as syringes comprise a longitudinal tip at their distal end (the extremity in the direction of injection, close to the patient skin), the longitudinal tip having a longitudinal channel for dispensing any material stored in the reservoir. However, this longitudinal tip does not allow parenteral administration by itself and must either comprise a staked needle or an adaptor allowing the connection of the syringe to a connector such as a needle hub or an intravenous (IV) line. Such an adaptor is a critical part for the safety of the injection and must be reversibly connectable to connectors and irreversibly secured to the longitudinal tip of the syringe. Indeed, it is essential for safety reasons that the adaptor and the connector are assembled together correctly and securely on the longitudinal tip of the syringe.

Connection of the adaptor with a connector is usually achieved by two cooperating threads, one being located on the inside of the adaptor and another one being located outside the proximal part of the connector, so that the needle or the intravenous line can be screwed into the adaptor prior to the injection. However, screwing of these two parts together often results in a significant pullout force between the tip and the adaptor, as some connectors apply a pressure on the tip and a counter pressure on the adaptor to achieve tight sealing. In addition, when a viscous drug is injected, a pullout force applied to the adaptor is created, as the connector inner diameter is smaller than the diameter of the tip longitudinal channel. Both phenomena may lead to the disconnection of the adaptor from the drug delivery device, which may affect patient and medical staff safety.

Finally, securely screwing the connector often results in applying a significant torque to the connector, the torque being transmitted to the adaptor; resulting in a risk that the adaptor ends rotate around the longitudinal tip. This may prevent a secured connection of the connector to the adaptor as it becomes difficult to ensure that the connector is fully screwed into the adaptor. Consequently, the connection between the adaptor and the longitudinal tip of the syringe has to resist against the pullout force as well as against the torque applied at the time of connection with a connector and/or at the time of injection. Indeed, the pullout of the adaptor from the syringe tip may lead to leakage of expensive medical composition but also to a non-accurate injection dose or, in extreme case, to projection of the drug or projection of the injection needle. Moreover, rotation of the adaptor with respect to the longitudinal tip may prevent an optimal connection with the connector and thus may also lead to leakages and/or needle stick injuries, as already mentioned.

Adaptors for connecting a drug delivery device to a connector are well known. These adaptors are usually secured around the longitudinal tip of the syringe by snap-fitting or friction force, for example by mechanical attaching means defined onto the longitudinal tip such as a groove or a ring. However, the incorporation of such attachment features on the longitudinal tip would require a complex molding tool in the case of a plastic drug delivery device or an additional forming step in the case of a glass drug delivery device, which may be difficult to control. Furthermore, a modified longitudinal tip may be sensitive to flaws and may potentially lead to tip breakage. Last but not least, an adaptor connected around a longitudinal tip by snap-fitting or friction force often demonstrates a limited torque resistance.

There is therefore a need for an adaptor showing both an optimal pullout force and torque resistance. There is also a need for an adaptor that is able to be mounted on a regular longitudinal tip without any further attaching means. There is finally a need for a drug delivery device provided with such adaptor. These needs are fulfilled by embodiments of the present disclosure.

BRIEF SUMMARY OF THE INVENTION

An embodiment of the present disclosure is an adaptor for a drug delivery device having a reservoir and a longitudinal tip, the longitudinal tip having an outer surface and a longitudinal channel for dispensing any material stored into the reservoir. The adaptor comprises a distal part defining a connecting ring intended to receive a connector, and a proximal part defining a mounting ring having an inner surface. The mounting ring is shaped and configured such that, when the adaptor is mounted around the longitudinal tip of the drug delivery device, an annular space is created between said inner surface of the mounting ring and said outer surface of the longitudinal tip, the annular space being further able to accommodate an adhesive layer in order to bond said adaptor to said longitudinal tip. An annular ring is provided at the distal extremity of the inner surface of the mounting ring.

Due to the annular space, in partly delimited by the annular ring, an adhesive layer introduced between the adaptor and the longitudinal tip allows for resisting any torque or pullout force submitted to the adaptor during use. Moreover, such an adaptor may be irreversibly bonded to a regular longitudinal tip, which is a longitudinal tip without any attaching means such as a groove or a ring.

In particular, in the adaptor of the disclosure, R1 being the radius of an inner diameter of the mounting ring and R2 being the radius of an inner diameter of the annular ring, R1 is greater than R2.

An aspect of the disclosure is an adaptor for a drug delivery device having a reservoir and a longitudinal tip, the tip having an outer surface and a longitudinal channel for dispensing any material stored into the reservoir, the adaptor comprising a distal part defining a connecting ring intended to receive a connector, and a proximal part defining a mounting ring intended to be connected to the outer surface of the longitudinal tip, said mounting ring having an inner surface, wherein an annular ring is provided at a distal extremity of the inner surface of the mounting ring, wherein R1 being the radius of an inner diameter of the mounting ring and R2 being the radius of an inner diameter of the annular ring, R1 is greater than R2.

The inner surface of the mounting ring and a proximal wall of the annular ring therefore define an inner annular recess of the mounting ring, said inner annular recess being open at its proximal end and closed at its distal end by the proximal wall of the annular ring. The inner annular recess has a radius R3 corresponding to R1-R2.

When the adaptor of the disclosure is mounted around the longitudinal tip of the drug delivery device, the inner annular recess allows creating an annular space between the inner surface of the mounting ring and the outer surface of the longitudinal tip. As will appear from the description below, the annular space is able to accommodate an adhesive layer in order to bond the adaptor to the longitudinal tip. In embodiments, the inner surface of the mounting ring comprises at least one protrusion such that, when the adaptor is mounted around the longitudinal tip of the drug delivery device, said at least one protrusion protrudes into said at least one annular space. In a preferred embodiment, the inner surface of the mounting ring comprises protrusions such that, when the adaptor is mounted around the longitudinal tip of the drug delivery device, the protrusions protrude into the annular space created between the mounting ring and the longitudinal tip. These protrusions may or may not contact the outer surface of the longitudinal tip and are intended to optimize the annular space in particular when it accommodates an adhesive layer. In particular, the protrusions are intended to optimize the inner structure of the inner annular recess and of the annular space, by creating within said inner annular recess and said annular space a plurality of partly separated volumes communicating with one another and each capable of receiving part of the adhesive intended to form the adhesive layer.

In embodiments, said at least one protrusion is chosen among, at least one continuous longitudinal rib, at least one segmented rib, transversal segments, at least one diagonal rib, bulbs or cylinders, T or crosses. The protrusions may consist in a variety of shapes, such as continuous or segmented longitudinal ribs, transversal segments, diagonal ribs, bulbs or crosses, at least one protrusion being required. The protrusions create volumes that communicate with one another so that, when a fluid adhesive is introduced in the annular space by the open proximal end of the inner annular recess, the adhesive flows and spreads so as to fill the plurality of volumes forming the annular space. When an adhesive layer is accommodated in the annular space, continuous or segmented longitudinal ribs provide an additional resistance to a torque applied onto the adaptor, while transversal segments bring an additional resistance to a pull out force applied to the adaptor. Diagonal ribs, bulbs and/or crosses bring an additional resistance to both torque and pull out force.

In embodiments, the inner surface of the mounting ring comprises protrusions in the form of longitudinal ribs. For example, the inner surface of the mounting ring comprises protrusions in the form of three longitudinal ribs projecting from the inner surface of the mounting ring. The longitudinal ribs may be regularly placed along a circumference of the inner surface. The longitudinal ribs may extend on the whole length of the mounting ring. In embodiments, the longitudinal ribs are continuous longitudinal ribs. In embodiments, the longitudinal ribs are segmented longitudinal ribs. Continuous or segmented longitudinal ribs may provide an additional resistance to a torque applied onto the adaptor when the adaptor is bonded to the longitudinal tip of the drug delivery device.

In embodiments, the inner surface of the mounting ring comprises protrusions in the form of transversal segments. Transversal segments may bring an additional resistance to a pull out force applied to the adaptor, when the adaptor is bonded to the longitudinal tip of the drug delivery device.

In embodiments, the inner surface of the mounting ring comprises protrusions in the form of three diagonal ribs. In embodiments, the inner surface of the mounting ring comprises protrusions in the form of bulbs or cylinders. In embodiments, the inner surface of the mounting ring comprises protrusions in the form of T or crosses.

The annular ring is useful to prevent adhesive from reaching the distal portion of the longitudinal tip, which thus remains clean for future medical use. In addition, the annular ring may be helpful as a centering means during the assembly of the adaptor of the present disclosure to the longitudinal tip of a drug delivery device.

In embodiments, wherein R1 being the radius of an inner diameter of the mounting ring and R2 being the radius of an inner diameter of the annular ring, R1 being greater than R2, the inner surface of the mounting ring and a proximal wall of the annular ring define an inner annular recess of the mounting ring, said inner annular recess being open at its proximal end and closed at its distal end by the proximal wall of the annular ring, said inner annular recess has a radius R3 corresponding to R1-R2, wherein R3 ranges from 0.3 to 0.5 mm.

In embodiments where the inner surface of the mounting ring comprises protrusions, the protrusions protrude into said inner annular recess of said mounting ring.

The adaptor is preferably made of a single piece of material to ensure optimal strength. Rigid plastic may be a material of choice for the same reason. Optionally, the adaptor may be made of a light-transmitting material to allow the detection of leaks and/or weak connections, when a connector is connected to the adaptor.

Another embodiment of the present disclosure is a drug delivery device comprising a reservoir for storing a material to be dispensed and a longitudinal tip having a longitudinal channel for dispensing any material stored in the reservoir. The drug delivery device further comprises an adaptor mounted around the longitudinal tip to allow the connection of a connector with the longitudinal channel, the adaptor being bonded to the longitudinal tip by an adhesive layer. This adhesive layer brings significant improvements when compared to prior-art adaptors. In particular, it allows reaching a high resistance to the torque and the pullout force applied to the adaptor. Furthermore, an irreversible bonding of the adaptor to the longitudinal tip of the drug delivery device may be achieved without any need of further attaching means. This avoids an additional manufacturing step to create attaching means and prevents weakening of the longitudinal tip, in particular when the drug delivery device is made of glass.

When the inner surface of the adaptor mounting ring comprises protrusions, these protrusions optimize the adherence strength of the adhesive layer in order to obtain improved resistance to the pull out force and/or the torque. The homogeneity of the adhesive layer may also be optimized due to these protrusions.

Before being used, a drug delivery device provided with an adaptor according to the present disclosure may be closed by a tip cap in order to prevent the stored material from escaping the reservoir during storage and transportation. Examples of such tip caps are described in the International application WO2015055608 and European patent EP1192965. Preferably, a drug delivery device closed by such a tip cap may have evidence of prior use means to make visible if such a drug delivery device has already been opened and is unsafe for injection. Such evidence of prior use means may comprise a shrinkable film such as disclosed in International application WO2010064074, or breakable tabs between the tip cap and the adaptor.

The adaptor bonded to the longitudinal tip of the drug delivery device shows a significant resistance to torque and pullout force that may be applied during handling and/or use.

Other advantageous embodiments of the present disclosure are described below.

BRIEF DESCRIPTION OF THE DRAWINGS

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 1:
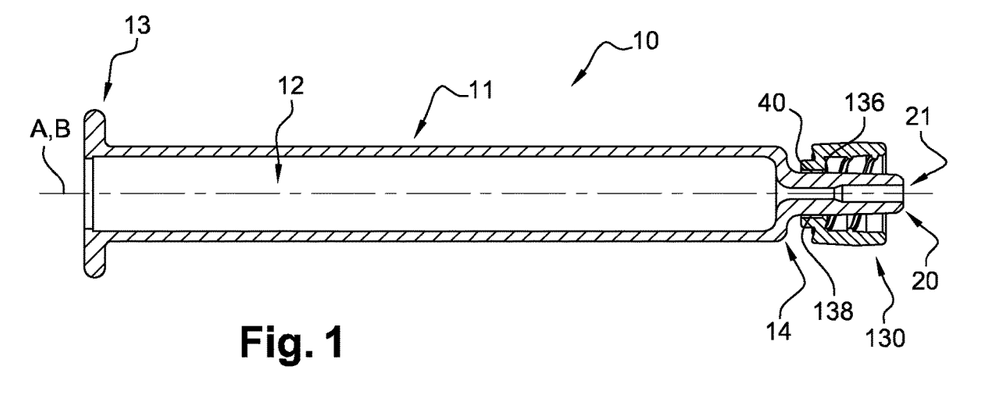
FIG. 1 discloses a drug delivery device according to the present disclosure.

FIG. 1 discloses an example of a drug delivery device 10 according to the present disclosure. The drug delivery device 10 has a longitudinal axis A and comprises a longitudinal barrel 11 defining a reservoir 12, the longitudinal barrel 11 having an open proximal end defining a flange 13 and a restricted distal end defining a longitudinal tip 20 with a longitudinal channel 21. The boundary between the longitudinal tip 20 and the barrel 11 defines a shoulder 14. An adaptor 130 having a longitudinal axis B and an annular ring 136 is mounted around the longitudinal tip 20 in such a way that an annular space 138 is created between the adaptor 130 and the longitudinal tip 20. Besides, an adhesive layer 40 is accommodated into the annular space 138 so as to bond the adaptor 130 onto the longitudinal tip 20. With reference to FIG. 1, when the adaptor 130 is bonded onto the longitudinal tip 20, the longitudinal axis B of the adaptor 130 is aligned on the longitudinal axis A of the drug delivery device 10.

Figure 2:
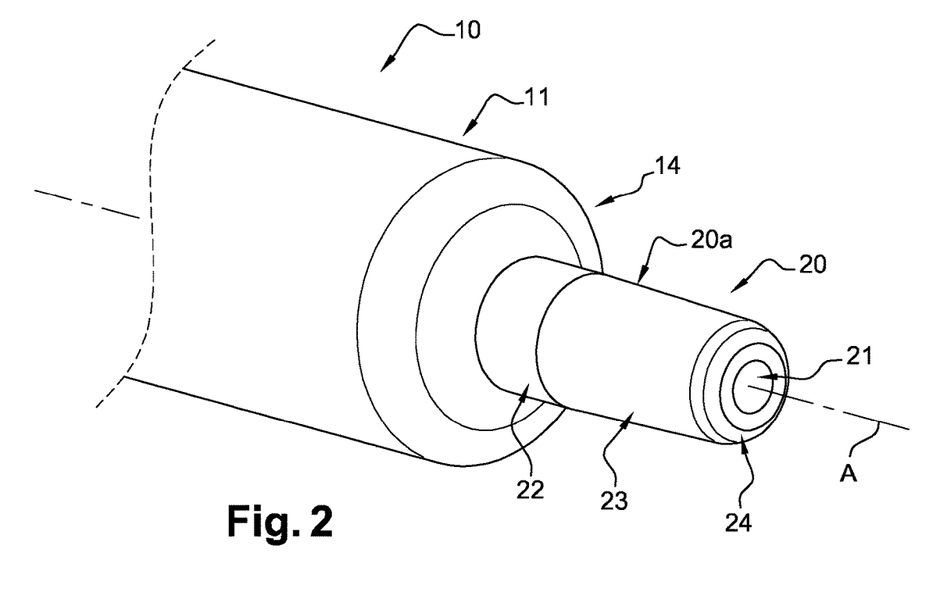
FIG. 2 is a magnified view of the longitudinal tip of a drug delivery device according to FIG. 1.

Referring to FIG. 2, the longitudinal tip 20 of the drug delivery device 10 has an outer surface 20a and globally a conical shape. More precisely, it comprises a cylindrical portion 22, located proximally to a conical portion 23. The longitudinal tip 20 defines a distal surface 24 that may be flat, beveled or curved. In another embodiment (as shown in FIG. 8C), the longitudinal tip 20 only comprises a conical portion 23 without any cylindrical portion 22.

Figure 3:
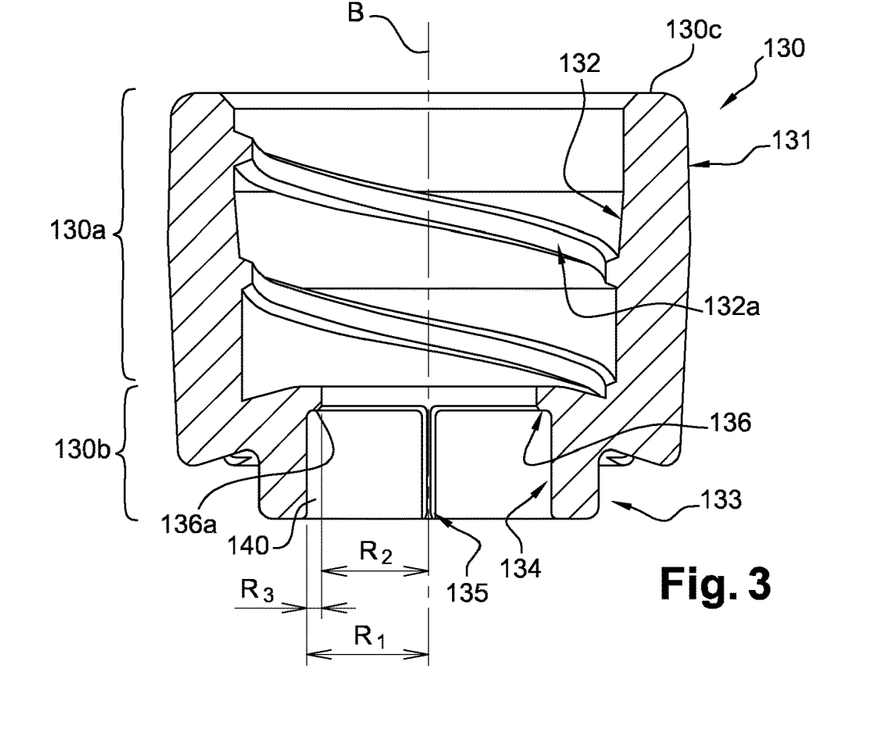
FIG. 3 discloses a cross-section view of an adaptor according to an embodiment of the present disclosure.
Figure 4:
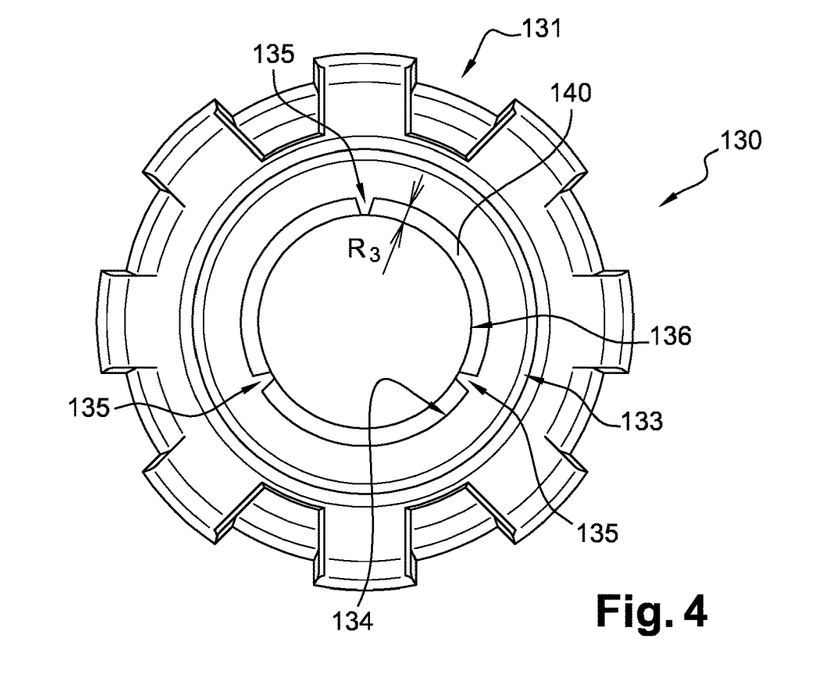
FIG. 4 discloses a rear view of the adaptor of FIG. 3.
Figure 5:
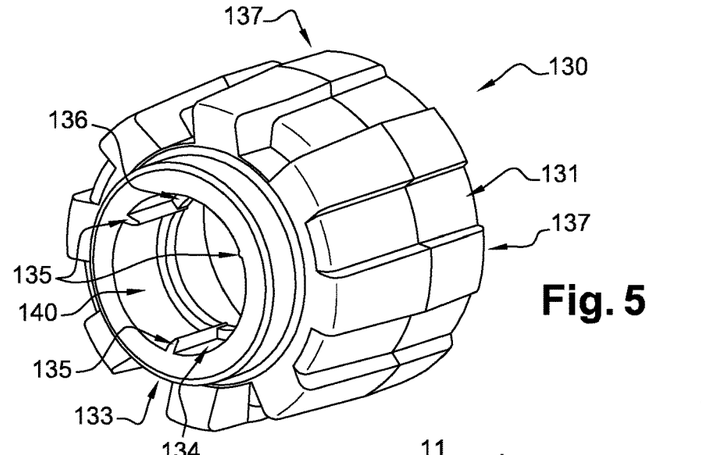
FIG. 5 discloses a perspective back view of the adaptor of FIG. 3.

An adaptor 130 according to a first embodiment of the present disclosure is disclosed in FIGS. 3 to 5.

The adaptor 130 comprises a distal part 130a, defining a connecting ring 131 having an inner surface 132. The inner surface 132 is provided with a thread 132a as a connecting member able to connect a connector (not shown), such as a needle or an intravenous line. Alternatively, these connecting members could be a bayonet system or a snapping system (not shown). The distal end of the connecting ring 131 defines the distal end 130c of the adaptor 130.

The adaptor 130 further comprises a proximal part 130b with a mounting ring 133 defining an inner surface 134. The inner surface 134 of the mounting ring 133 of the adaptor 130 is provided with protrusions in the form of three longitudinal ribs 135 projecting from the inner surface 134 of the mounting ring 133 (only one is visible in FIG. 3). Preferably, the longitudinal ribs 135 are regularly placed along a circumference of the inner surface 134. Preferably, the longitudinal ribs 135 extend on the whole length of the mounting ring 133. On the example shown, the longitudinal ribs 135 are continuous longitudinal ribs.

Additionally, an annular ring 136 is further defined at the distal extremity of the inner surface 134, at the boundary between the mounting ring 133 and the connecting ring 131. In FIGS. 3 to 5, said annular ring 136 contacts the longitudinal ribs 135, however in other examples, the longitudinal ribs 135 may be proximally spaced from the annular ring 136.

With reference to FIG. 3, are shown the radius R1 of an inner diameter of the mounting ring 133 and the radius R2 of an inner diameter of the annular ring 136. As appears from this figure, R1 is greater than R2.

With reference to FIGS. 3-5, the inner surface 134 of the mounting ring 133 and a proximal wall 136a of the annular ring 136 therefore define an inner annular recess 140 of the mounting ring 133, said inner annular recess 140 being open at its proximal end and closed at its distal end by the proximal wall 136a of the annular ring 136. The inner annular recess 140 has a radius R3 corresponding to R1-R2.

In embodiments, R3 ranges from 0.3 to 0.5 mm.

With reference to FIGS. 3-5, the longitudinal ribs 135 protrude into the inner annular recess 140.

On its outer surface, the adaptor 130 may have an embossed design, showing for example more or less thick longitudinal projections 137 (see FIG. 5) in order, for instance, to ease its gripping. The longitudinal projections 137 present on the outer surface of the adaptor as shown in FIG. 5, are an example of an embossed design intended to provide an easy handling of the adaptor 130 by the user when a connector is about to be screwed onto the drug delivery device of the present disclosure, even with gloves or wet hands.

The adaptor 130 can be made of any rigid polymer adapted to medical use, such as high density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and combinations thereof. To simplify its manufacturing, the adaptor 130 preferably consists of a single piece of material, preferably of a light-transmitting material.

Figure 6:
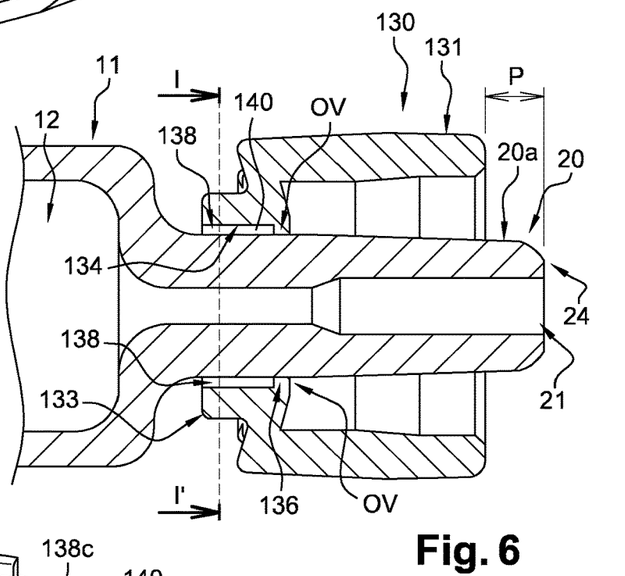
FIG. 6 is a cross-section view of the adaptor of FIG. 3 when assembled on a longitudinal tip of a drug delivery device.
Figure 7:
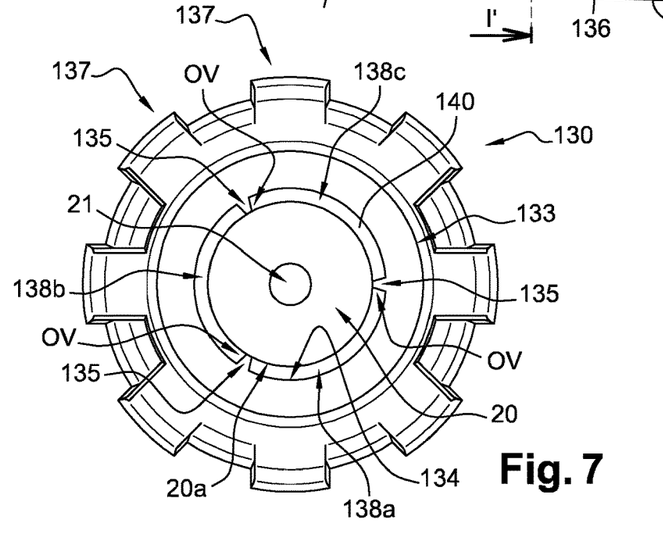
FIG. 7 is a cross-section view of the adaptor of FIG. 6 along the plane I-I'.
Figure 8A:
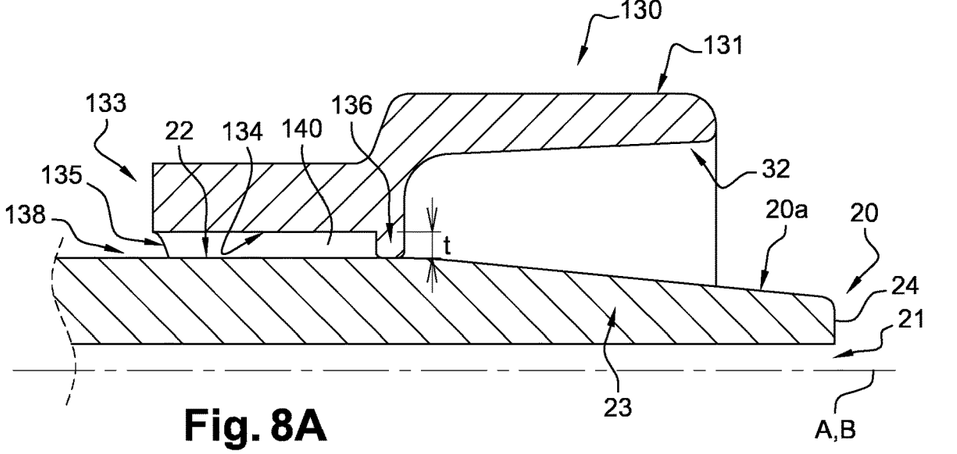
FIGS. 8A to 8C are cross-section views of different examples of the adaptor of FIG. 3 assembled on the longitudinal tip of the drug delivery device of FIG. 2.
Figure 8B:
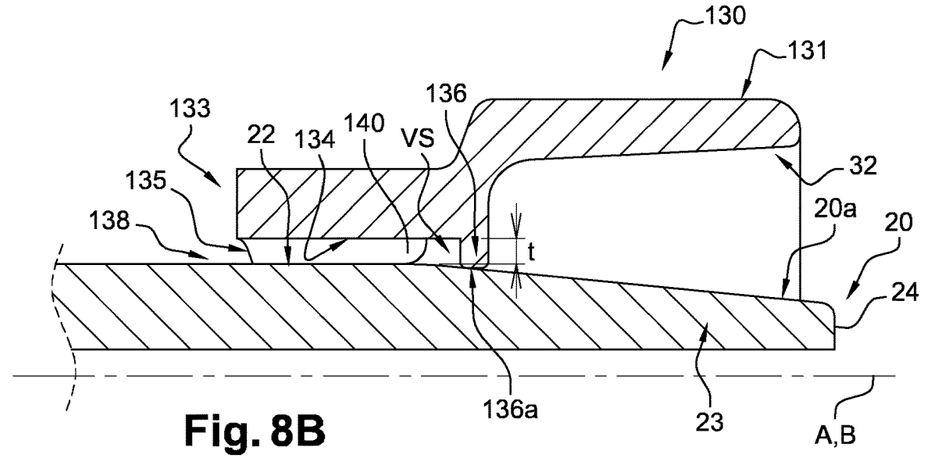
Figure 8C:
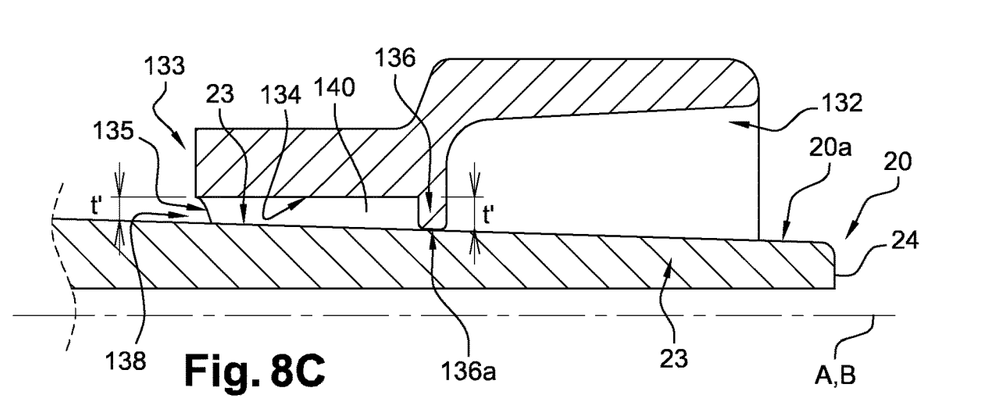
Figure 9:
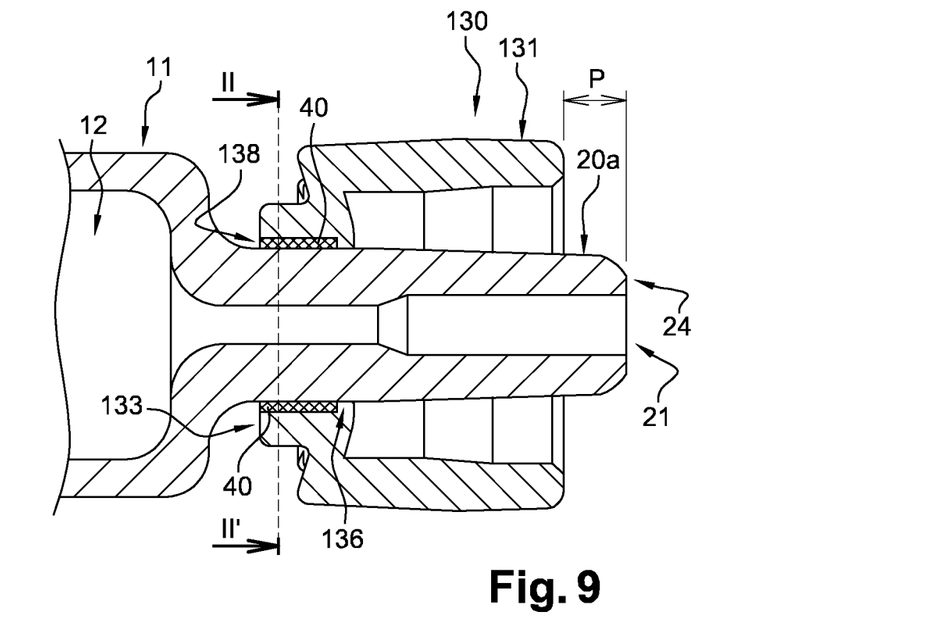
FIG. 9 is a cross-section view of the adaptor of FIG. 3 bonded to the longitudinal tip of a drug delivery device.

The adaptor 130 is intended to be mounted on the longitudinal tip 20 of a drug delivery device 10, such that the distal surface 24 of said drug delivery device 10 extends further from the connecting ring 131 in the distal direction, in particular of a distance P (see FIGS. 6 and 9). As shown in FIGS. 6, 7 and 8A-8C, the mounting ring 133 is shaped and configured such as to create an annular space 138 between the inner surface 134 of the mounting ring 133 and the outer surface 20a of the longitudinal tip 20. This annular space 138 is able to accommodate an adhesive layer 40 in order to irreversibly bond the adaptor 130 to the longitudinal tip 20. In particular, the inner annular recess 140 of the mounting ring 133 allows creating said annular space 138.

In FIG. 8A, the mounting ring 33 is mounted on the cylindrical portion 22 of the tip 20, the conical portion 23 of the conical tip being available for any connection. The longitudinal ribs 135 and the annular ring 136 may or may not be in contact with the outer surface 20a of the longitudinal tip 20. Preferably, at least one of the longitudinal ribs 135 or the annular ring 136 is in contact with the outer surface 20a of the longitudinal tip 20. If required, at least one of the longitudinal ribs 135 or the annular ring 136 may show an interference-fit with the outer surface 20a of the longitudinal tip 20. For example in FIG. 6, the interference fit between the annular ring 136 and the outer surface 20a of the longitudinal tip 20 is represented on the FIGS. 6 and 7 as an overlap OV of the annular ring on the longitudinal tip 20. This interference fit may be useful for a friction force pre-assembly of the adaptor 130 onto the longitudinal tip 20 before irreversible bonding with an adhesive layer 40. As visible in FIG. 7, an overlap OV between the longitudinal ribs 135 and the outer surface 20a of the longitudinal tip 20 is visible and may also be useful for a friction force pre-assembly. As shown in FIG. 7, the longitudinal ribs 135 segment the inner annular recess 140, and the longitudinal ribs 135 therefore segment the annular space 138 into three cavities (138a, 138b, 138c), each cavity having a proximal opening and being closed by two longitudinal ribs 135 and a portion of the annular rib 136.

Alternatively, the mounting ring 133 of the adaptor 130 may be mounted on the cylindrical portion 22 and the conical portion 23 of the longitudinal tip 20. As visible in FIG. 8B, the longitudinal ribs 135 may face or contact the cylindrical portion 22 while the annular ring 136 may face or contact the conical portion 23 of the longitudinal tip 20. In this FIG. 8B, the annular ring 136 and the longitudinal ribs 135 do not contact with each other and are separated by a void space VS. Such a configuration may be useful to expand the area of the annular space 138 in which the adhesive layer 40 is intended to be accommodated. In other words, with such a configuration, an adhesive layer 40 with a larger area may be accommodated between the outer surface 20a of the longitudinal tip 20 and the inner surface 134 of the mounting ring 133, when compared to the example of FIG. 8A. Preferably, the inner surface 134 of the mounting ring 133 is substantially parallel to the outer surface 20a of the longitudinal tip 20, such as to create an annular space 138 with a constant thickness (t), as visible in FIGS. 8A and 8B. In such cases where the inner surface 134 of the mounting ring 133 is substantially parallel to the outer surface 20a of the longitudinal tip 20, and the annular space 138 has a constant thickness (t), the volume of the annular space 138 may be substantially equal to the volume of the inner annular recess 140.

In another alternative shown in FIG. 8C, the longitudinal tip 20 is not provided with a cylindrical portion 22 but only with a conical portion 23. In this example, the inner surface 134 of the mounting ring 133 has a straight profile while the outer surface 20a of the longitudinal tip 20 has a sloped profile, thus creating an annular space 138 with a progressive thickness (t'). In such a case, the volume of the annular space 138 may be substantially less than the volume of the inner annular recess 140 of the mounting ring 133.

For example, for bonding the adaptor 130 to the longitudinal tip 20, an adhesive is introduced in the annular space 138. Due to the longitudinal ribs 135, the adhesive is homogeneously distributed into the annular space 138 to form a uniform adhesive layer 40 (see FIGS. 9 and 10) segmented by said longitudinal ribs 135. The annular ring 136 may act as a barrier for the adhesive as it prevents the adhesive from reaching the distal portion of the longitudinal tip 20 which thus remains clean for future medical usage. The adhesive may be dispensed onto the adaptor 130, prior or posterior to the adaptor being positioned around the longitudinal tip 20.

The adhesive may be any material adapted to bond parts in the medical field. In particular, the adhesive may be chosen between a hot-melt adhesive and glue, for example glue with an acrylate base. The bonding area may be comprised between 20 to 40 mm$^2$ and the thickness of the adhesive layer 40 may be comprised between 0.3 and 0.5 mm.

The adhesive may be cured by any method adapted to form an adhesive layer 40 (see FIG. 9-10) permanently bonded to the outer surface 20a of the longitudinal tip 20 and to the inner surface 134 of the adaptor 130. The curing method may be selected according to the specific type of adhesive used and may be chosen among gamma-irradiation, UV-irradiation, heat curing, cooling or drying, and the like. Prior to this curing step, the interference fit between the outer surface 20a of the longitudinal tip 20 and the annular ring 136 and/or the longitudinal ribs 135 may be useful to temporarily maintain the adaptor 130 onto the longitudinal tip 120 at the correct position, thus avoiding any disconnection due to the vibrations generated by the assembly process.

Figure 10:
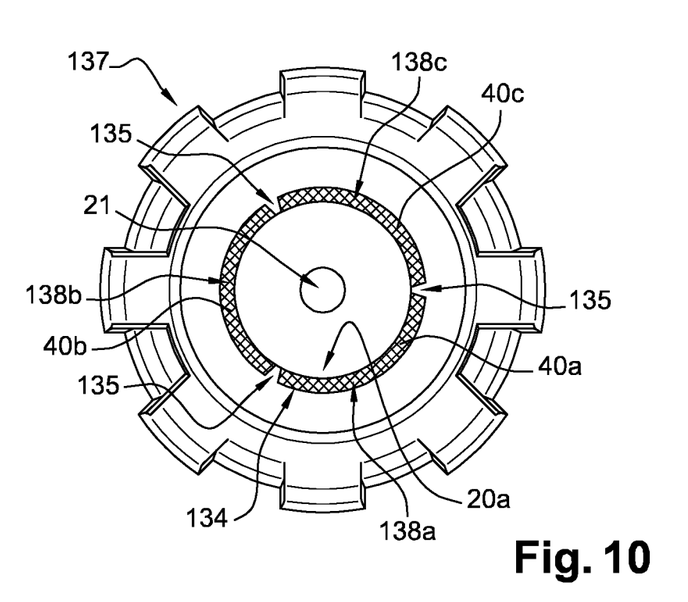
FIG. 10 is a cross-section view of the adaptor of FIG. 9 along the plane II-IF.

At the end of this assembly process, the adaptor 130 is irreversibly bonded to the longitudinal tip 120 of a drug delivery device 110 by an adhesive layer 40 accommodated into an annular space 138, as shown in FIGS. 9 and 10. Due to this adhesive layer 40, the adaptor 130 may be bonded around the longitudinal tip 20 without any need for a groove or a ring on the outer surface 20a of the longitudinal tip 20 as it would otherwise normally be required by the adaptors of the prior art. This greatly simplifies the manufacturing process of such a drug delivery device, especially for glass-made drug delivery devices. Furthermore, the chemical bonding obtained with the presence of the adhesive layer 40 allows for reaching a superior resistance to the torque and to the pullout force that is usually applied to the adaptor 130 when a connector is connected to the connecting ring 131 of the adaptor 130.

Referring to FIG. 10, the adhesive layer 40 is segmented by the longitudinal ribs 135 into three portions (40a, 40b, 40c), which allow resisting the important torque applied when a connector is connected to the drug delivery device 10 via the adaptor 130. When such a torque is applied, the longitudinal ribs 135 reduce the shear stress between the adhesive and either the outer surface 20a of the longitudinal tip 120 or the inner surface 134 of the mounting ring 133 of the adaptor 130. The longitudinal ribs 135 thus act as mechanical stops by blocking any potential rotational movement of the adaptor 130 against the adhesive layer 40 which contributes to increase the torque resistance of an adaptor 130 bonded to the longitudinal tip 20 of a drug delivery device 10 by an adhesive layer 40.

Figure 11A:
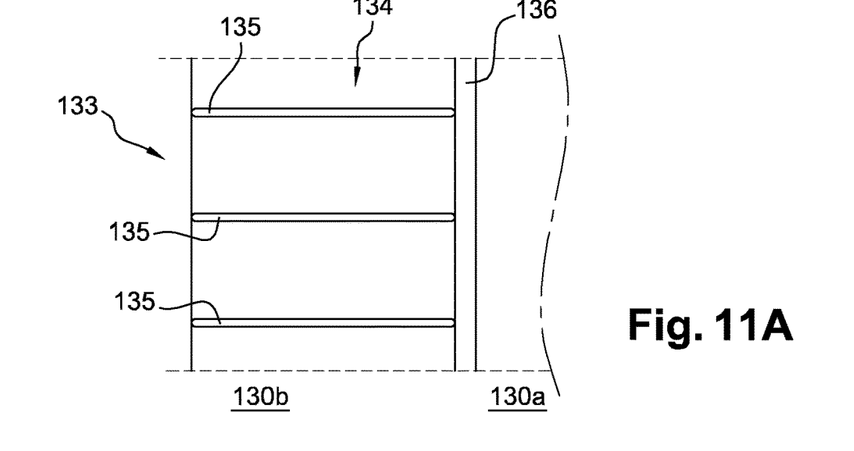
FIGS. 11A-11F are the flat projections of the inner surface of the mounting rings of adaptors according to different embodiments of the adaptor of the present disclosure.

In other embodiments, the protrusions may adopt other shapes to achieve different technical effects. FIG. 11A represents the flat projection of the inner surface 134 of the mounting 133 of the adaptor 130 according to the first embodiment of the present disclosure (FIGS. 3-5) and is given for reference.

Figure 11B:
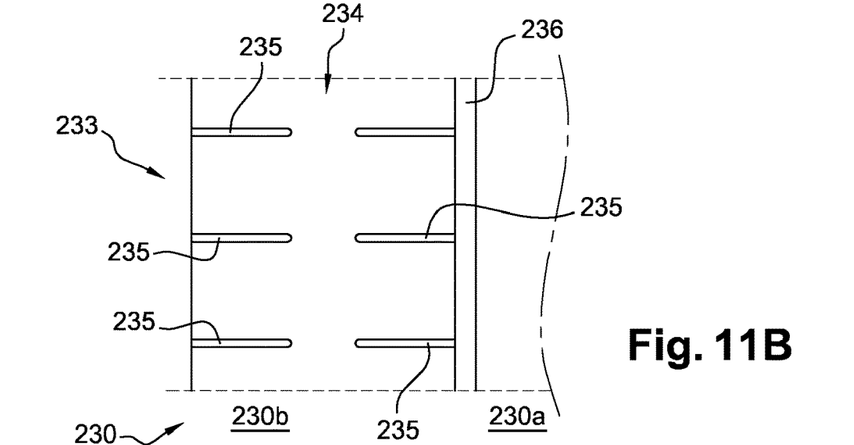

FIG. 11B shows the flat projection of the inner surface 234 of the mounting ring 233 of an adaptor 230 according to another embodiment of the present disclosure. This adaptor 230 is similar to the previously described adaptor 130 and differs in that the inner surface 234 comprises protrusions in the form of segmented longitudinal ribs 235. Such protrusions 235 may be useful to optimize the homogeneity of the adhesive layer 40 in the second step of the bonding process as previously described. As shown in FIG. 11B, an annular ring 236 is provided at the distal extremity of the inner surface 234 of the mounting ring 233.

Figure 11C:
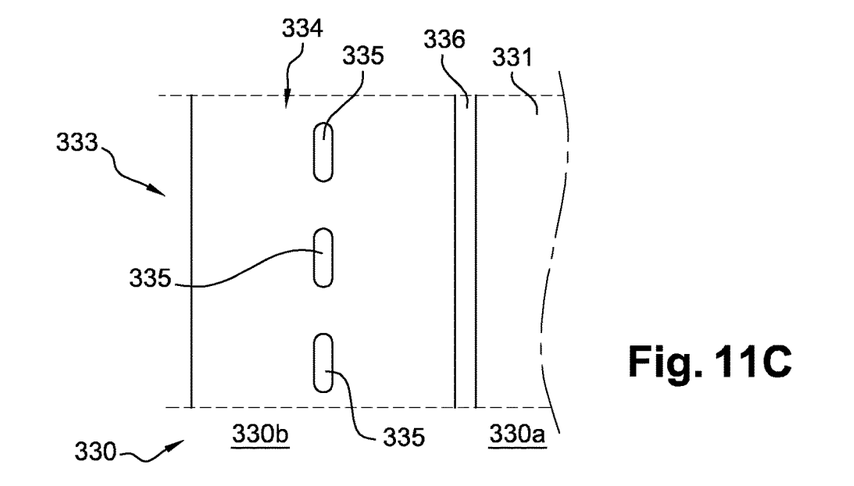

FIG. 11C represents the flat projection of the inner surface 334 of the mounting ring 333 of an adaptor 330 according to another embodiment of the present disclosure. This adaptor 330 is similar to the previously described adaptor 130 but differs in that the inner surface 334 is provided with protrusions in the form of transversal segments 335. Such protrusions 335 may be useful to reduce the shear stress between the adhesive and the inner surface 334 or the outer surface 20a of the longitudinal tip 20 when the adaptor 330 is submitted to a pullout force, for example when a connector is connected to the connecting ring 331. When the adaptor 330 is assembled onto the longitudinal tip 20 of a drug delivery device 10 by an adhesive layer 40, the transversal segments 335 may thus act as mechanical stops by blocking any potential pullout movement of the adaptor 330 against the adhesive layer 40 which contributes to increase the pullout resistance of the adaptor 330. As shown in FIG. 11C, an annular ring 336 is provided at the distal extremity of the inner surface 334 of the mounting ring 333.

Figure 11D:
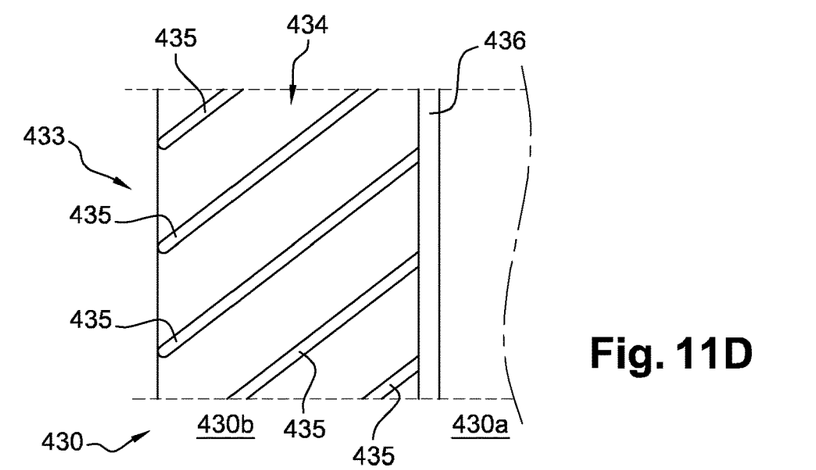

FIG. 11D represents the flat projection of the inner surface 434 of the mounting ring 433 of an adaptor 430 according to another embodiment of the present disclosure. This adaptor 430 is similar to the previously described adaptor 130 but differs in that the inner surface 434 is provided with protrusions in the form of three diagonal ribs 435, at least one diagonal rib 435 being required. Because of their diagonal positioning, such protrusions 435 may be useful to provide for a mechanical stop blocking both pullout movements and torque when the adaptor 430 is bonded by an adhesive layer 40 to the longitudinal tip 20 of a drug delivery device 10. Such protrusions 435 may also help to obtain a homogeneous adhesive layer 40, for example by a rotation of the adaptor 430 during the introduction of the adhesive in the second step of the above-described assembly process. As shown in FIG. 11D, an annular ring 436 is provided at the distal extremity of the inner surface 434 of the mounting ring 433.

Figure 11E:
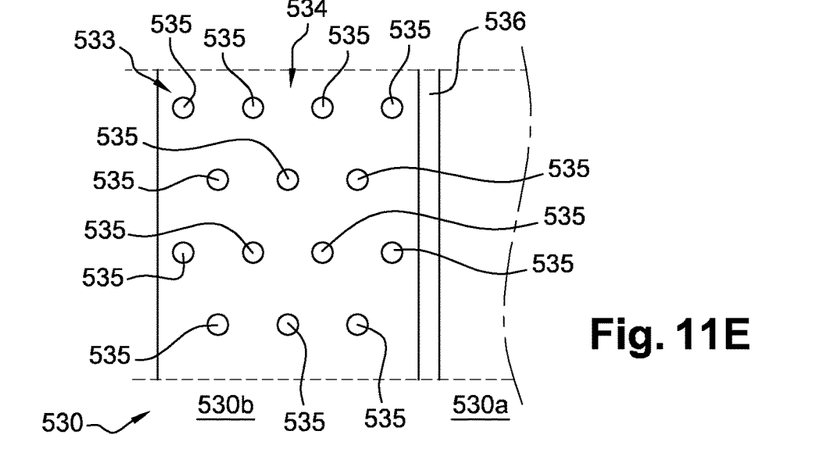

FIG. 11E is the flat projection of the inner surface 534 of the mounting ring 533 of an adaptor 530 according to another embodiment of the present disclosure. This adaptor 530 is similar to the previously described adaptor 130 but differs in that the inner surface 534 is provided with protrusions in the form of bulbs or cylinders 535. Similarly to the diagonal ribs 435, the bulbs 535 may be useful to provide for a mechanical stop blocking both pullout movements and torque when the adaptor 530 is bonded by an adhesive layer 40 to the longitudinal tip 20 of a drug delivery device 10. Such protrusions 535 may also help to obtain a homogeneous adhesive layer 40, for example by distributing the adhesive by percolation in the annular space 438 in the second step of the above-mentioned process. As shown in FIG. 11E, an annular ring 536 is provided at the distal extremity of the inner surface 534 of the mounting ring 533.

Figure 11F:
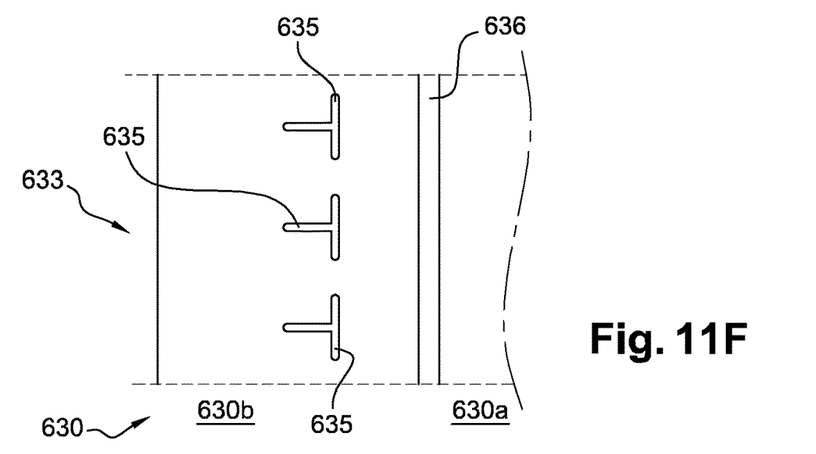

FIG. 11F is the flat projection of the inner surface 634 of the mounting ring 633 of an adaptor 630 according to another embodiment of the present disclosure. This adaptor 630 is similar to the previously described adaptor 130 but differs in that the inner surface 634 is provided with protrusions in the form of T or crosses 635. Similarly to the diagonal ribs 435 and the bulbs 535, the crosses 635 may be useful to provide for a mechanical stop in order to block both pullout movements and torque when the adaptor 630 is bonded by an adhesive layer 40 to the longitudinal tip 20 of a drug delivery device 10. As shown in FIG. 11F, an annular ring 636 is provided at the distal extremity of the inner surface 634 of the mounting ring 633.

In the embodiment of FIGS. 11B to 11F, the protrusions (235, 335, 435, 535, 635) protrude in the respective corresponding annular space created between the inner surfaces (234, 334, 434, 534, 634) and the outer surface of the longitudinal tip, and may or may not contact the outer surface 20a of the longitudinal tip 20, when the corresponding adaptors (230, 330, 430, 530, 630) are bonded to the longitudinal tip 20 of a drug delivery device 10. Furthermore, these embodiments are provided with an annular rib similar to the annular rib 136 of the adaptor 130. As applicable, all individual features that are shown in the individual embodiments can be combined and/or exchanged with each other without departing from the scope of the disclosure.

The annular space created between the mounting ring of the adaptor and the outer surface 20a of the longitudinal tip 20 may thus be optimized by protrusions to provide for an additional resistance to pullout and/or torque of the adhesive layer 40. Furthermore, some protrusions may also help for the homogeneity of the adhesive layer 40, thus avoiding weaknesses in the adhesive layer 40.

Moreover, with the adaptors according to the above-mentioned embodiments, the longitudinal tip 20 of the drug delivery device 10 is not required to define further attaching means such as an annular groove or a ring, which may be difficult to manufacture, in particular in the case of glass-made drug delivery devices. Finally, as the glass forming process may lead to important dimensional tolerances, specifically at the shoulder 14 between the longitudinal barrel 11 and the longitudinal tip 20, it is particularly valuable that the adaptor is exclusively bonded around the longitudinal tip 20, without any direct contact with the longitudinal barrel 11 of the drug delivery device 10.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An adaptor for a drug delivery device having a reservoir and a longitudinal tip having an outer surface and a longitudinal channel for dispensing any material stored into the reservoir, the adaptor comprising:
    a distal part defining a connecting ring intended to receive a connector;
    a proximal part defining a mounting ring having an inner surface, the mounting ring being shaped and configured such that, when the adaptor is mounted around the longitudinal tip of the drug delivery device, at least one annular space is created between the inner surface of the mounting ring and the outer surface of the longitudinal tip, the at least one annular space being able to accommodate an adhesive layer in order to bond the adaptor to the longitudinal tip; and
    an annular ring provided at a distal extremity of the inner surface of the mounting ring,
    wherein the inner surface of the mounting ring further comprises at least one protrusion such that, when the adaptor is mounted around the longitudinal tip of the drug delivery device, the at least one protrusion protrudes into the at least one annular space, wherein the at least one protrusion being in the form of longitudinal ribs, and wherein the longitudinal ribs extend a whole length of the mounting ring.

2. The adaptor according to claim 1, wherein the inner surface of the mounting ring comprises protrusions in the form of three longitudinal ribs projecting from the inner surface of the mounting ring.

3. The adaptor according to claim 2, wherein the longitudinal ribs are equidistantly placed along a circumference of the inner surface.

4. The adaptor according to claim 1, wherein the longitudinal ribs are continuous longitudinal ribs.

5. The adaptor according to claim 1, wherein the longitudinal ribs are segmented longitudinal ribs.

6. The adaptor according to claim 1, wherein R1 being the radius of an inner diameter of the mounting ring and R2 being the radius of an inner diameter of the annular ring, R1 being greater than R2, said inner annular recess having a radius R3 corresponding to R1-R2, wherein R3 ranges from 0.3 to 0.5 mm.

7. The adaptor according to claim 1, wherein the adaptor is formed of rigid plastic.

8. The adaptor according to claim 1, wherein the adaptor if formed of a single piece of material.

9. The adaptor according to claim 1, wherein the adaptor is formed of a light-transmitting material.

10. A drug delivery device comprising the adaptor according to claim 1.

11. The drug delivery device according to claim 10, wherein the adaptor is irreversibly bonded to the longitudinal tip by an adhesive layer accommodated into the annular space.

12. The drug delivery device according to claim 11, wherein the adhesive layer has a thickness of at least 0.3 mm.

13. The drug delivery device according to claim 11, wherein said adhesive layer covers an area of at least 20 $mm^2$ of the outer surface.

14. The drug delivery device according to claim 11, wherein said at least one protrusion protrudes into said adhesive layer.

15. The drug delivery device according to claim 11, wherein the adaptor is exclusively bonded to the drug delivery device by the adhesive layer.

16. The drug delivery device according to claim 10, wherein the inner surface of the mounting ring is substantially parallel to the outer surface of the longitudinal tip.

17. The drug delivery device according to claim 10, wherein the longitudinal tip is made of glass.

18. The drug delivery device according to claim 10, wherein the longitudinal tip does not have any mechanical attaching means such as an annular groove or a ring.

* * * * *

UNITED STATES PATENT AND TRADEMARK OFFICE
CERTIFICATE OF CORRECTION

PATENT NO. : 11,833,339 B2
APPLICATION NO. : 17/096676
DATED : December 5, 2023
INVENTOR(S) : Marc Flippe et al.

It is certified that error appears in the above-identified patent and that said Letters Patent is hereby corrected as shown below:

In the Claims

Column 12, Line 24, Claim 8, delete "if" and insert -- is --

Signed and Sealed this
Twenty-fifth Day of June, 2024

Katherine Kelly Vidal
*Director of the United States Patent and Trademark Office*